United States Patent [19]
Tsao et al.

[11] Patent Number: 5,846,919
[45] Date of Patent: Dec. 8, 1998

[54] RAPID OPHTHALMIC DISINFECTION SOLUTION USING SALT AND GLYCOL AND/OR LOWER ALKANOL AND SURFACTANT

[75] Inventors: Fu-Pao Tsao, Lawrenceville; Susan Ann Littlefield, Norcross; John Harlan Stone, Conyers, all of Ga.

[73] Assignee: CIBA Vision Corporation, Duluth, Ga.

[21] Appl. No.: 721,772

[22] Filed: Sep. 25, 1996

Related U.S. Application Data

[60] Continuation of Ser. No. 382,322, Mar. 22, 1995, abandoned, which is a division of Ser. No. 116,820, Sep. 3, 1993, Pat. No. 5,411,597, which is a continuation of Ser. No. 928,524, Aug. 11, 1992, abandoned, which is a continuation of Ser. No. 776,711, Oct. 15, 1991, abandoned, which is a continuation of Ser. No. 456,059, Dec. 21, 1989, abandoned, which is a continuation-in-part of Ser. No. 304,746, Jan. 31, 1989, abandoned.

[51] Int. Cl.$^6$ .............................. A61L 2/18; C11D 3/20; C11D 3/04
[52] U.S. Cl. .......................... 510/112; 510/384; 514/839; 514/840; 422/28; 134/26; 134/42
[58] Field of Search ..................... 510/112, 384; 514/839, 840; 422/28; 34/26, 42

[56] References Cited

U.S. PATENT DOCUMENTS

| | | | |
|---|---|---|---|
| 4,046,706 | 9/1977 | Krezanoski | 252/106 |
| 4,124,520 | 11/1978 | Schwalley et al. | 252/106 |
| 4,315,828 | 2/1982 | Church | 252/153 |
| 4,336,152 | 6/1982 | Like et al. | 252/106 |
| 4,421,665 | 12/1983 | Lloyd et al. | 252/106 |
| 4,507,219 | 3/1985 | Hughes | 252/118 |
| 4,543,200 | 9/1985 | Sherman | 252/106 |
| 4,655,957 | 4/1987 | Chromecek et al. | 252/174.23 |
| 4,784,790 | 11/1988 | Disch et al. | 252/174.12 |
| 4,908,147 | 3/1990 | Tsao et al. | 252/106 |

FOREIGN PATENT DOCUMENTS 0001888  10/1979  European Pat. Off. .

*Primary Examiner*—Jerry D. Johnson
*Attorney, Agent, or Firm*—Michael U. Lee; R. Scott Meece

[57] ABSTRACT

A disinfection solution, primarily for use in conjunction with contact lenses is disclosed comprising an amount of a pharmaceutically acceptable ionic salt which is equivalent in ionic strength to at least 5% w/v sodium chloride, at least one of a $C_{2-6}$ alkanol and a $C_{3-8}$ alkylene glycol, a pharmaceutically acceptable surfactant, optionally a buffer, and water.

12 Claims, No Drawings

RAPID OPHTHALMIC DISINFECTION SOLUTION USING SALT AND GLYCOL AND/ OR LOWER ALKANOL AND SURFACTANT

This application is a continuation of application Ser. No. 08/382,322, filed Mar. 22, 1995, now abandoned; which is a divisional of application Ser. No. 08/116,820, filed Sep. 3, 1993, now U.S. Pat. No. 5,411,597; which is a continuation of application Ser. No. 07/928,524, filed Aug. 11, 1992 now abandoned; which is a continuation of application Ser. No. 07/776,711, filed Oct. 15, 1991 now abandoned; which is a continuation of application Ser. No. 07/456,059, filed Dec. 21, 1989 now abandoned; which is a continuation-in-part of application Ser. No. 07/304,746, filed Jan. 31, 1989 now abandoned.

FIELD OF THE INVENTION

The invention is in the area of contact lens care products, particularly solutions used to clean and disinfect contact lenses.

BACKGROUND OF THE INVENTION

Disinfection solutions for use in conjunction with contact lenses have been in use essentially as long as contact lenses have been available to the public. There is a large diversity in the makeup of the various known solutions, primarily due to the fact that to date no single solution has been found to meet all of the parameters desired in a single solution. For example, currently commercially available solutions such as ReNu Disinfectant (Bausch & Lomb), Optisoft (Alcon), and Optifree (Alcon) which offer low irritancy and/or hypersensitivity require a minimum of four (4) hours soaking to disinfect. Solutions such as Flexcare contain thimerosol which has been particularly problematical as a disinfecting or preservative agent. Because of these problems there has been an attempt to avoid thimerosol as an antimicrobial agent.

A second, and not small consideration, is contact lens material/solution comparability. Heat disinfection is not a practical alternative for use with high water content soft contact lenses. Some lenses entrap or react with various components of the disinfection solution making it impossible to utilize such solutions with those lenses. For this reason, proper patient compliance with lens/solution match-up directions is essential to mainintaing contact lenses properly. Yet experience has shown that patient compliance with lens and solution manufacturer directions is not adhered to by a significant, although small patient population. Hence, there has been an effort to develop a disinfection solution which is generally useful for most, if not all contact lenses currently available.

Finally, not all disinfectant solutions are suitably effective against the entire range of microbial organisms which are of concern in the contact lens field. One such organism where disinfectants and preservatives have had limited success is Acanthamoeba. The present invention solution is effective against the cyst as well as the trophozite stage of these protozoa.

OBJECTS OF THE INVENTION

One object of the invention is to provide a contact lens disinfecting solution which will be non-irritating to the patient after following a simple, easy to carry out disinfecting regimen.

A second object of the invention is to provide a one step cleaning and disinfecting solution meeting the foregoing object.

A third object is to provide a contact lens disinfection solution having compatability with essentially all currently available contact lenses.

A fourth object of the invention is to provide a disinfection solution which is effective against a wide range of ocular pathogens including Acanthamoeba.

SUMMARY OF THE INVENTION

Surprisingly, the foregoing objects and others are achieved by a disinfection solution comprising
 a) at least one of a $C_{2-6}$ alkanol and a $C_{3-8}$ alkylene glycol;
 b) an amount of a pharmaceutically acceptable contact lens compatable inorganic salt which is equivalent in toxicity to a 5%–20% sodium chloride solution;
 c) optionally a pharmaceutically aceptable, contact lens comptable amphoteric surfactant; optionally a pharmaceutically acceptable, contact lens compatable pH regulating agent or buffer;
 e) optionally a pharmaceutically acceptable, contact lens compatable viscosity enhancing agent; and
 f) water.

It should be emphasized here that the invention is also applicable beyond the contact lens disinfection and preservative field and may be used anywhere a disinfecting solution treatment or preserved solution would be useful provided only that the subject material to be treated is not adversely affected by the solution components. For these purposes, the invention solution need not be contact lens compatable or even pharmaceutically acceptable. The only important features in such a case are that the solution contain a tonicity building agent in an amount equivalent to a 5% or more concentrated solution of sodium chloride and at least one of (a) a $C_{2-6}$ alkanol and (b) a $C_{3-8}$ alkylene glycol. Typical non-contant lens disinfecting applications for which such solutions are useful include: lens case cleaner and disinfectant, topical medical composition, cosmetic, facial cleaner, hand cleaner, disinfecting soaps such as surgical soap, shampoo, household disinfectant, and industrial disinfectant, laboratory disinfectant, dental and medical equipment disinfectant, acne cleaning and disinfecting treatments, insect bite disinfection, for minor skin itching and rashes and wound healing applications. It is also suitable as a rapid in-office contact lens disinfecting/cleaning regimen.

DETAILED DESCRIPTION OF THE INVENTION

In its broadest sense, the instant invention is a disinfection solution comprising at least three components.
 (a) a tonicity building agent in an amount such that a solution thereof in water would have a tonicity equivalent to that of a 5% or more concentrated aqueous sodium chloride solution;
 (b) at least one of a $C_{2-6}$ alkanol and a $C_{3-8}$ alkylene glycol; and
 (c) an appropriate solvent.

Additional components which may be present include a surfactant (for enhanced cleaning capability and some antimicrobical effect if a quaternary ammonium compound); a pH regulator; and a viscosity builder. Other components may also be present which are typical for the type of formulation useful for the purpose to which the inventive solution is being put. Hence if the solution is to be a cleanser where surface scratching is not of concern, agents such as silicon dioxide may be present as well.

The formulations of the invention are typically used by contacting the surface to be treated with the formulations, rubbing up the formulation on the surface from 5–30 seconds and rinsing the treated surface. In terms of the preferred use, contact lens disinfection, the solution is placed on the lens in the same manner as any other cleaner or disinfectant for contact lenses, rubbed lightly for 5–30 seconds and rinsed with water or normal saline as appropriate.

In the typical formulation of the invention, the $C_{3-8}$ alkylene glycol is present from about 10% to about 50% by weight, preferably about 15% to about 40% by weight, still more preferably about 17% to about 25% by weight, most preferably about 21% by weight of the entire formulation.

The $C_{3-8}$ alkylene glycol is preferably selected from 1,2 or alpha,omega glycols such as 1,2-propylene glycol, 1,2-butylene glycol, 1,2-pentylene glycol, 1,2-hexylene glycol, 1,3-propylene glycol, 1,4-butylene glycol, 1,5-pentylene glycol, and 1,6-hexylene glycol. Also preferably, the $C_{3-8}$ alkylene glycols are $C_3$ or $C_4$ alkylene glycols such as 1,2-propylene glycol, 1,3-propylene glycol, 1,2-butylene glycol, 1,3-butylene glycol, 1,4-butylene, 2,3-butylene glycol, 2-methyl-1,2-propylene glycol, and 2-methyl-1,3-propylene glycol. Most preferably, the $C_{3-6}$ alkylene glycol is 1,2-propylene glycol or 1,3-propylene glycol. Another highly preferable glycol is 1,6-hexylene glycol.

The surfactant when present, is usually present in an amount of about 2% to about 15% by weight, preferably about 3% to about 12% by weight, most preferably about 5% by weight to about 10% by weight of the entire formulation. However, less than 2% may also be used. The surfactant is selected from virtually any ocularly acceptable surfactant including non-ionic, anionic, and amphoteric surfactants, and furthermore, if the ultimate use is not ophthalmic, the components need not be pharmaceutically acceptable. However, it is preferably selected from a) compounds of formula I

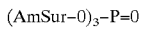

(I)

wherein the group AmSur is of the formula

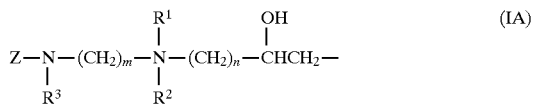

(IA)

wherein each of $R^1$–$R^3$ is independently lower alkyl, hydroxy lower alkyl, or carboxy lower alkyl, Z is an alkanoyl of 6–18 carbon atoms or Z together with one of $R^1$ and $R^3$ is methylene substituted by $C_5$–$C_{17}$ alkyl; n and m are each independently 1–4. Where AmSur contains a net charge, a suitable ocularly acceptable counter ion, such as chloride, is also present in an appropriate amount. The three AmSur radicals can be the same or different, but preferably all three AmSur radicals in one molecule are the same;

b) compounds of the formula

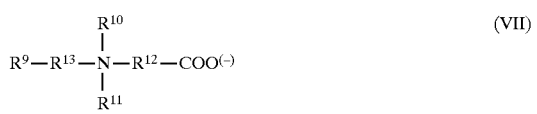

(VII)

wherein $R^9$ is alkyl of 5–17 carbon atoms or a $C_{6-20}$ alkanoylamino; each of $R^{10}$ and $R^{11}$ is independently lower alkyl, hydroxy lower alkyl, or carboxy lower alkyl; $R^{12}$ is an alpha,omega-alkylene of 1 to 6 carbons which is unsubstituted or substituted by lower alkyl, hydroxy, or hydroxy lower alkyl; and $R^{13}$ is alpha,omega $-C_1$–$C_5$ alkylene;

c) compounds of the formula

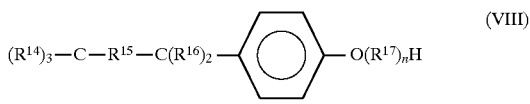

(VIII)

wherein each $R^{14}$ and each $R^{16}$ is independently $C_{1-4}$ alkyl; $R^{15}$ is $C_{1-4}$ alpha,omega-alkylene; each $R^{17}$ is independently

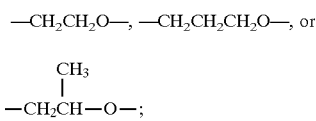

and n is 3–18; and d) compounds of the formula

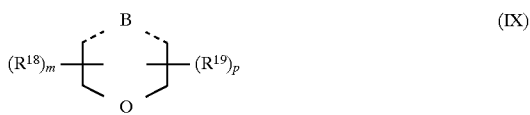

(IX)

wherein B is a $C_{1-4}$-alpha,omega-alkylene; p is an integer 0 to d-1; m is an integer of from 0 to (d-p-1); d=4–7; each $R^{18}$ is independently H or a $C_{1-4}$ alkyl which is unsubstituted or substituted by at least one $R^{19}$; each $R^{19}$ is independently a hydroxy which is free, etherified by $R^{20}$, or esterified by $R^{21}$; each $R^{20}$ is a $C_{2-4}$ straight or branched oxyalkylene orpoly ($C_{2-4}$ straight or branched oxyalkylene), the terminal oxygen of which is bound to H or $R^{21}$; and each $R^{21}$ is independently an acyl of a $C_{2-24}$ alkanoic acid or a $C_{4-24}$ alkenoic acid; provided that in each compound of formula IX there is at least one free hydroxy group, and at least one $R^{21}$ group. Compounds of formula VII are typically available from Miranol under the names Mirataine® and Miranol®; compounds of formula VIII are available under the names Igepal CA®, Polytergent® and Triton X®; and compounds of formula IX are available under the Span® and Tween® brand names.

Preferably the compounds of Formula I are selected from

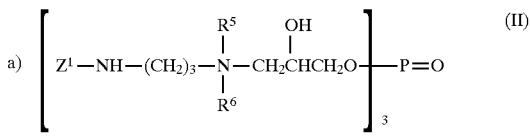

(II)

wherein $R^5$ and $R^6$ are each $C_1$–$C_4$ alkyl and $z^1$ is $C_6$–$C_{18}$ alkanoyl;

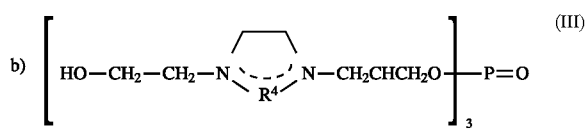

(III)

wherein $R^4$ is methylene substituted by $C_5$–$C_{17}$ alkyl; and

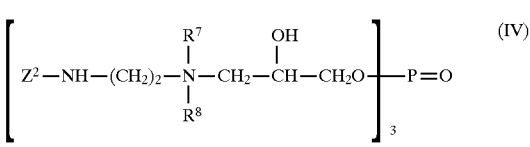

(IV)

wherein $Z^2$ is $C_{12}$–$C_{14}$ alkyl, one of $R^7$ and $R^8$ is carboxy lower alkyl, and the other of $R^7$ and $R^8$ is hydroxy lower alkyl.

Compounds of formulae II–IV are available from Mona Industries, New Jersey under the series trade name Monaquat®-P. More preferably, within formulae II–IV, are the compounds a) [Z²—NH—(CH₂)₃N⁽⁺⁾(CH₃)₂—CH₂CH(OH)CH₂O]₃-P=O 3Cl⁻(V) wherein Z² is C₆–C₁₇ alkanoyl (available under the name Monaquat®P-TC) or C₁₂–C₁₄ alkanoyl (available under the name Monaquat®P-TD);

b) compounds of formula III, available under the name Monaquat®P-TZ; and

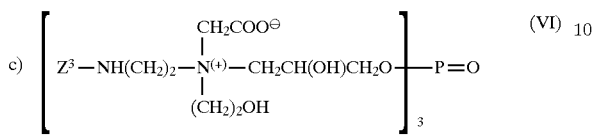

wherein Z³ is C₁₂–C₁₄ alkanoyl, available under the name Monaquat®P-TL. The most preferable compound of the Monaquat®P series for use in the instant invention is Monaquat®P-TL, i.e. compounds of formula VI. Compounds within formula II generally are disclosed in U.S. Pat. Nos. 4,209,449 and 4,336,385, the disclosures of which are included herein by reference.

The lower alkanol, when present, is present from about 2% to about 30% by weight, preferably about 10% to about 20% by weight, most preferably about 16% by weight of the entire formulation. Lower alkanol is selected from $C_{1-7}$, preferably $C_{2-6}$ straight or branched alkanols, such as methanol, ethanol, n-propanol, isopropanol, n-butanol, sec-butanol and t-butanol, more preferably isopropanol or ethanol, most preferably isopropanol.

When both the glycol and alkanol components are present, they may individually be present in amounts below the foregoing minimums provided that the sum of the % fractions of the two total at least 1.0. The % fraction is defined as the actual % present divided by the minimum % previously stated. For example, a solution having 1% alkanol has a % fraction of 0.5 (1%/2%) for alkanol. Such a solution would then require at least a % fraction of glycol of 0.5, or at least 5% glycol component in the solution. Similarly a 1% glycol containing solution, a % fraction of 0.1 (1%/10%), would require at least an alkanol % fraction of 0.9, or 1.8% alkanol. Simply put, if the glycol is present in X% and the alkanol Y% than the minimums of the ranges would be the solutions for the equation $$\frac{Y\%}{\text{minimum of alkanol alone}} + \frac{X\%}{\text{minimum of glycol alone}} \geq 1.0.$$

The pH regulating component can be added as a preformed buffer or can be formed in situ. If the pH of the solution without this component is suitable it is not required, although its presence is desirable. Any ocularly compatible inorganic or organic acid or base or organic buffer system can be used. Typical buffer systems include the well known phosphate or borate systems. Other suitable systems include, without limitation, the lactate, pyruvate, citrate, tartrate, acetate, and laurate systems.

Most preferably the buffer system used will have a pK in the range of the desired pH range so as to maximize the buffering capacity. The most preferable buffer system is lactic acid/lactate which is preferably formed in situ by the addition of lactic acid alone. In the case of lactic acid/lactate as the pH adjuster (i.e. buffer), the combined lactic acid and lactate are preferably present from about 0.5–about 2% by weight of the solution based on lactate ion, more preferably about 0.75% to about 1.5%, most preferably about 1.1% of the solution.

The pH of the final solution may be advantageously in the range of 3–7.0, preferably 5–7, more preferably about 5.5 to about 6. The lower pHs, while suitable, are advantageous in that minimum disinfecting time is shortened over the same composition at higher pH, but disadvantageous in that reestablishment of neutral pH is necessary before a lens is placed back on the eye.

The tonicity builder is present in an amount which yields a tonicity equivalent to sodium chloride solutions (w/v%) in the range of 5.0% to 20% sodium chloride, preferably in the range of 8.5% to 17.5% sodium chloride, more preferably about 10% to 15% sodium chloride, most preferably about 12.5% sodium chloride. The most preferable compound for use as a tonicity builder is sodium chloride, although any compatible (ocularly compatible if ophthalmic device disinfection is the intended usage) inorganic or organic salt which does not interfere with the other components will do.

The overall solution tonicity should preferably be at least equivalent to 7.5% to 12.5%, more preferably about 10% aqueous NaCl. The tonicity builder amounts stated above can be adjusted by those of ordinary skill to have the solution meet these overall more preferable limits. Typical tonicity builders include ophthalmically acceptable alkaline metal or alkaline earth metal halide, phosphate, carbonate, sulfate, etc.

The viscosity enhancer is present to help increase the solution viscosity to preferably not greater than 100 cps, more preferably not greater than 80 cps, still more preferably not greater than 30 cps, most preferably not greater than 10 cps. Any ocularly compatible non-ionic or quaternay ammonium viscosity enhancer is suitable. Examples of non-ionic viscosity enhancers utilizable on the instant invention include: lower alkyl celluloses (i.e. methyl cellulose, ethyl cellulose, etc.) hydroxy lower alkyl celluloses (i.e. hydroxy methyl cellulose, hydroxy ethyl cellulose, hydroxy propyl cellulose, etc.), poloxamers, reverse poloxamers, ethoxylated ethylene diamines, etc.

Preferably, the viscosity enhancer is a cellulose ether, more preferably hydroxy lower alkyl cellulose, most preferably hydroxy ethyl cellulose, such as HECQP 4400 available from Union Carbide. In a most preferred solution, hydroxy ethyl cellulose is the viscosity enhancer and is present in an amount of about 0.1% by weight of the solution.

The solution of the invention can be formulated from the above components in any manner known in the art. For example the solid components can be dissolved directly in the water, either simultaneously or sequentially, with liquid components being added thereto either before or after the solid components. Alternatively the solid components can be triturated with one or more non-water liquid components and this mixture diluted with an appropriate amount of water. It is preferable to dissolve all of the components (other than the viscosity enhancer) first and then mix the viscosity enhancer into this solution. Variations of the above will be apparent to the ordinarily skilled formulator.

The instant solutions are rapid cleaning and disinfecting solutions for a wide range of contact lens and other materials. Typically, one applies a few drops of the solution to the lens material and rubs it for 5–30 seconds, preferably 10–20 seconds, more preferably about 15 seconds. This is repeated for the opposite surface. The lens is then rinsed in normal or water saline for at least 5 seconds, preferably 10–20 seconds, most preferably 15 seconds, and stored in normal saline for at least 20 seconds, preferably 30 seconds to 1.5 minutes, most preferably 1 minute. Longer storing times are acceptable, but not necessary. The instant solution can be used in the above method for all types of contact lenses; soft lenses, hard lenses, and rigid gas permeable lenses. Such lens materials for which the instant solution can be used include bufilcon A, cobufocon A, crofilcon A, deltafilcon A, deltafilcon B, dimefilcon A, droxifilcon, etafilcon A, hefilcon A, hefilcon B, itafocon A, lidofilcon A, mafilcon A, ocufilcon A, ocufilcon B, optacryl 60, pasifocon A, pasifocon B, pasifocon C, perfilcon A, phemfilcon A, polymacon, porofocon B, silafilcon A, silafocon A, tefilcon, tetrafilcon A, vifilcon A, PMMA, silicone/MMA copolymer, MMA/glyceryl methacrylate copolymer, and poly t-butyl stryene. Others will be apparent to those of ordinary skill.

Having fully described the invention, the following Examples are presented to exemplify but do not limit the invention.

EXAMPLE 1

15.72 isopropyl alcohol, 10.00 g of sodium chloride, 10.00 g of Pluronic F-127 (poloxamer 407), and 15.00 g of Miranol H2M (concentrate) are dissolved in 49.3 g of water (deionized) and the pH is adjusted with concentrated HCl to result in an invention solution having a pH of 6.0. Microbiological data is presented in Example 43.

EXAMPLE 2

Example 1 is followed except that the amount of Minanol H2M is 20.00 g and water is 44.3 g. Microbiological data is present in Table V.

EXAMPLES 3 THROUGH 16

Examples 3–16 are prepared in the same manner as Example 1 but using the amounts set forth in Table I below. In each of these Examples, 15.7 g of isopropyl alcohol is employed and the pH is 6.0. Microbiological data is present in Table V.

TABLE I

| Example No. | NaCl (g) | Pluronic F-127 (g) | Miranol H2M (g) | H2O (g) |
|---|---|---|---|---|
| 3 | 10.0 | 5.0 | 10.0 | 59.3 |
| 4 | 10.0 | 5.0 | 15.0 | 54.3 |
| 5 | 10.0 | 5.0 | 20.0 | 49.3 |
| 6 | 7.0 | 15.0 | 10.0 | 52.3 |
| 7 | 7.0 | 15.0 | 15.0 | 47.3 |
| 8 | 7.0 | 15.0 | 20.0 | 39.3 |

TABLE I

| Example No. | NaCl (g) | Pluronic F-127 (g) | Miranol H2M (g) | H2O (g) |
|---|---|---|---|---|
| 9 | 7.0 | 10.0 | 10.0 | 57.3 |
| 10 | 7.0 | 10.0 | 15.0 | 52.3 |
| 11 | 7.0 | 10.0 | 20.0 | 47.3 |
| 12 | 7.0 | 5.0 | 10.0 | 62.3 |
| 13 | 7.0 | 5.0 | 15.0 | 57.3 |
| 14 | 7.0 | 5.0 | 20.0 | 52.3 |
| 15 | 5.0 | 15.0 | 10.0 | 54.3 |
| 16 | 10.0 | 15.0 | 10.0 | 49.3 |

EXAMPLES 17–19

Examples 17 to 19 are prepared in accordance with Example 1 except that 16 g of Isopropyl alcohol was used, the pH was 6.0 and the amounts set forth in Table II were employed.

TABLE II

| Example No. | NaCl (g) | Pluronic F-127 (g) | Miranol H2M (g) | H2O (g) |
|---|---|---|---|---|
| 17 | 12.0 | 10.0 | 10.0 | 52.0 |
| 18 | 12.0 | 15.0 | 10.0 | 47.3 |
| 19 | 10.0 | 10.0 | 10.0 | 49.3 |

EXAMPLE 20

Example 20 is the same as Example 19 except the amount of isopropyl alcohol was 20 g.

EXAMPLES 21–23

Example 21 to 23 were prepared in accordance with Example 1 using hexylene glycol in place of the Miranol H2M. 1 g of Pluronic L-31, 2 g of Lactic Acid and pH was 3.0 in place of the pluronic, acid, and pH in Example 1. The remaining ingredients were used in the amounts shown in Table III.

TABLE III

| Example No. | Hexylene Glycol (g) | Isopropyl Alcohol (g) | NaCl (g) | Propylene Glycol (g) |
|---|---|---|---|---|
| 21 | 0 | 20 | 10 | 0 |
| 22 | 0 | 30 | 10 | 0 |
| 23 | 0 | 40 | 10 | 0 |

EXAMPLES 24–31

Examples 24–31 are prepared in accordance with Example 1 except that hexylene glycol and/or Betaine are used in place of the Miranol H2M, Lactic Acid (2 g) is used in place of hydrochloric acid and the pH is 3.0. 1 g Betaine is present in each of Examples 24–31. The remaining ingredients are set forth in Table IV.

TABLE IV

| Example No. | Hexylene Glycol (g) | Isopropyl Alcohol (g) | NaCl (g) | Propylene Glycol (g) |
|---|---|---|---|---|
| 24 | 0 | 20 | 10 | 0 |
| 25 | 0 | 30 | 10 | 0 |

TABLE IV

| Example No. | Hexylene Glycol (g) | Isopropyl Alcohol (g) | NaCl (g) | Propylene Glycol (g) |
|---|---|---|---|---|
| 26 | 0 | 40 | 10 | 0 |
| 27 | 30 | 10 | 10 | 0 |
| 28 | 30 | 0 | 12 | 0 |
| 29 | 30 | 0 | 10 | 0 |
| 30 | 0 | 20 | 12 | 0 |
| 31 | 0 | 30 | 12 | 0 |

EXAMPLE 32

The solutions of Examples 1–16 were tested for their effectiveness against *S.epidermidis* as follows:

The organism was cultured to a density of $10^8$/ml in nutrient broth. 0.01 Ml of this innoculum was pippetted onto each side of a vifilicon A (55% water) soft contact lens and left in contact therewith for 5 minutes. The innoculated lens was then allowed to soak in 2 ml of solution for 0.5 to 1 minute and the number of remaining viable organisms was determined. The results are reported in Table V below.

TABLE V

| Solution of Example | No. of Surviving Viable Organisms (S. epidermidis) | % Reduction in contamination |
|---|---|---|
| 1 | $5.45 \times 10^2$ | 99.94% |
| 2 | $8.65 \times 10^2$ | 99.91% |
| 3 | 0 | 100% |

TABLE V

| Solution of Example | No. of Surviving Viable Organisms (S. epidermidis) | % Reduction in contamination |
|---|---|---|
| 4 | 50 | 99.995% |
| 5 | 50 | 99.995% |
| 6 | $6.6 \times 10^2$ | 99.934% |
| 7 | $1 \times 10^2$ | 99.99% |
| 8 | $6.2 \times 102$ | 99.94% |
| 9 | 0 | 100% |
| 10 | 0 | 100% |
| 11 | 10 | 99.999% |
| 12 | 0 | 100% |
| 13 | 25 | 99.997% |
| 14 | $1.5 \times 10^2$ | 99.98% |
| 15 | $7.6 \times 10^2$ | 99.92% |
| 16 | 0 | 100% |

EXAMPLE 33

Solutions of the Examples set forth below were tested for effectiveness against Acanthamoeba castelanii cysts as follows:

A $10^7$ cyst pellet was dissolved in 10 ml of test solution to result in a $10^6$ cyst/ml concentration in test solution. At the times specified below, 1 ml was withdrawn and diluted with 49 ml of saline to result in a cyst concentration of $2 \times 10^4$ cyst/ml. 0.1 Ml of this diluted solution was then added to 10 ml of nutrient media so that the entire nutrient media began with a $2 \times 10^3$ cyst population. The innoculated nutrient media were cultured for 3 weeks at which point effectiveness was assessed as (a) total kill (−) or (b) partial or no kill (+). The results are reported in Table VI below.

TABLE VI

| Solution Example No. | Exposure Time (min.) | | | | |
|---|---|---|---|---|---|
| | 1 | 2 | 3 | 4 | 5 |
| 9 | + | − | − | − | − |
| 19 | + | − | − | − | − |
| 17 | − | − | − | − | − |
| 21 | + | | | − | |
| 22 | + | | | − | |
| 23 | + | | | − | |
| 24 | + | | | − | |
| 25 | + | | | − | |
| 26 | + | | | − | |
| 27 | − | | | − | |
| 28 | − | | | − | |

TABLE VI-continued

| Solution Example No. | Exposure Time (min.) | | | | |
|---|---|---|---|---|---|
| | 1 | 2 | 3 | 4 | 5 |
| 29 | + | | | − | |
| 30 | + | | | − | |
| 31 | + | | | − | |

We claim:

1. A contact lens polymeric material cleaning and disinfecting solution, comprising:

(a) x percent by weight of a $C_3$–$C_8$ alkylene glycol and y percent of a $C_2$–$C_6$ alkanol, wherein x and y are each independently 0 to 50 and satisfy the equation (x/10 +y/2>1.0);

(b) an amount of about 2 weight percent to about 15 weight percent of an ophthalmic device material-compatible surfactant;

(c) an amount up to about 2 weight percent of a pH adjusting or regulating agent;

(d) an amount of tonicity builder sufficient to raise the solution tonicity to at least the equivalent of a 5 weight percent or more sodium chloride solution;

(e) an amount of viscosity-enhancing agent; and (f) an ophthalmologically acceptable solvent, wherein said composition is capable of simultaneously disinfecting and cleaning said contact lens polymeric material when contacted for a period less than about 60 seconds.

2. The solution of claim 1, wherein said surfactant and said viscosity-enhancing agent are the same substance.

3. The solution of claim 1 wherein said surfactant is selected from the group consisting of poly(oxypropylene) poly(oxyethylene)s, polyethyleneglycols, polypropyleneglycols, polypropyleneglycol-buteths, polypropyleneglycol oleates, polypropylene-pareths, tetrahydroxypropylethylenediamine, and ceteareths.

4. The solution of claim 1 wherein said viscosity enhancing agent is selected from the group consisting of poly (oxypropylene)poly(oxyethylene)s, polyethyleneglycols, polypropyleneglycols, polypropyleneglycol-buteths, polypropyleneglycol oleates, polypropylene-pareths, tetrahydroxypropylethylenediamine, ceteareths, nitrilotriacetic acid salts, disodium ethylenediaminotetracetate salts, and pentetate salts.

5. A composition for simultaneously cleaning and disinfecting contact lenses, comprising:

(a) 5 to 20 weight percent sodium chloride;

(b) 2 to 15 weight percent surfactant;

(c) x to 50 weight percent of an alkylene glycol having between 3 and 8 carbon atoms;

(d) y to 30 weight percent of a lower alkanol having 2 to 6 carbon atoms, wherein x and y are defined by the equation $x/10+y/2 \geq 1.0$;

(e) 0 to 2 weight percent pH regulating agent;

(f) a viscosity enhancing agent; and (g) an ophthalmologically acceptable solvent;

wherein said composition has a pH of 5 to 7, and wherein said composition is capable of disinfecting and cleaning a contact lens when applied by rubbing said composition with said lens over a period of less than about 60 seconds.

6. The solution of claim 5 wherein said alkylene glycol is propylene glycol or hexylene glycol; said alkanol is ethanol or isopropanol; said surfactant is of the formula

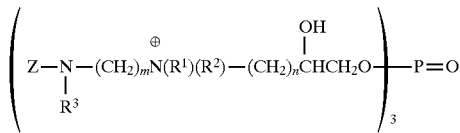

wherein each of $R^1$ to $R^3$ is independently lower alkyl, hydroxy lower alkyl, or carboxy lower alkyl, Z is $C_6$–$C_{18}$ alkanoyl or Z, together with one of R' and $R^3$, is methylene substituted by $C_5$–$C_{17}$ alkyl, and n and m are each 1–4 in association with sufficient ions of counter charge to result in a net compound charge of zero;

said pH adjusting or regulating agent is selected from a) phosphoric acid, boric acid, lactic acid and citric acid, b) an ophthalmically acceptable salt thereof, c) a mixture of said acid and said salt of said acid, d) an ophthalmically acceptable inorganic acid and e) an ophthalmically acceptable inorganic base;

said viscosity enhancer is selected from hydroxy-lower alkyl-cellulose, hydroxy-lower alkanoyl cellulose, lower alkyl-cellulose, lower alkanoyl cellulose, carboxy-lower alkyl-cellulose.

7. The solution of claim 5 wherein said alkylene glycol is propylene glycol; said lower alkanol is isopropylene alcohol; said surfactant is of the formula

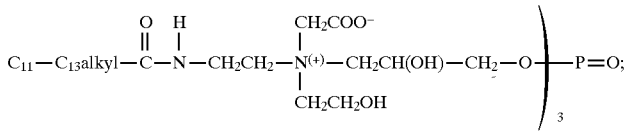

said pH adjusting or regulating agent is lactic acid; and said viscosity enhancer is hydroxy ethyl cellulose.

8. The solution of claim 5 wherein said alkylene glycol is present in an amount of about 21% by weight; said lower alkanol is present in an amount of about 16% by weight; said surfactant is present in an amount of about 5% by weight; said pH adjusting or regulating agent is present in an amount of about 1.1% by weight; and said viscosity enhancer is present in an amount of about 0.1% by weight.

9. The composition of claim 5 wherein said surfactant is selected from a) a compound of formula I

wherein each group AmSur is independently of the formula

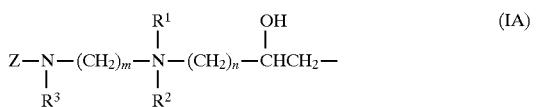

wherein each of $R^1$–$R^3$ is independently lower alkyl, hydroxy lower alkyl, or carboxy lower alkyl;

Z is an alkanoyl of 6–18 carbon atoms or Z together with one of $R^1$ and $R^3$ is methylene substituted by $C_5$–$C_{17}$ alkyl; n and m are each independently 1–4;

b) a compound of the formula

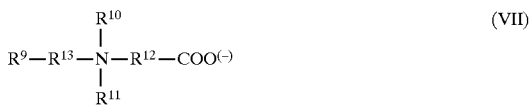

wherein $R^9$ is alkyl of 5–17 carbon atoms or a $C_{6-20}$ alkanoylamino; each of $R^{10}$ and $R^{11}$ is independently lower alkyl, hydroxy lower alkyl, or carboxy lower alkyl; $R^{12}$ is an alpha,omega-alkylene of 1 to 6 carbons which is unsubstituted or substituted by lower alkyl, hydroxy, or hydroxy lower alkyl; and $R^{13}$ is alpha,omega-$C_1$–$C_5$ alkylene;

c) a compound of the formula

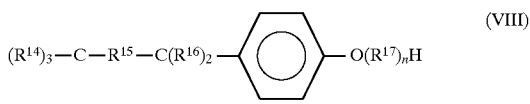

wherein each $R^{14}$ and each $R^{16}$ is independently $C_{1-4}$ alkyl; $R^{15}$ is $C_{1-4}$ alpha,omega-alkylene; each $R^{17}$ is independently —$CH_2CH_2O$—, —$CH_2CH_2CH_2O$—, or

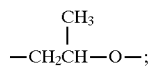

and n is 3–18; and d) a compound of the formula

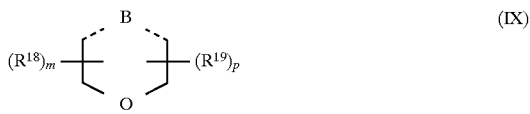

wherein B is a $C_{1-4}$-alpha,omega-alkylene; p is an integer 0 to d-1; m is an integer of from 0 to (d-p-1); d=4–7; each $R^{18}$ is independently H or a $C_{14}$ alkyl which is unsubstituted or substituted by at least one $R^{19}$; each $R^{19}$ is independently a hydroxy which is free, etherified by $R^{20}$, or esterified by $R^{21}$; each $R^{20}$ is a $C_{2-4}$ straight or branched oxyalkylene or poly($C_{2-4}$ straight or branched oxyalkylene), the terminal oxygen of which is bound to H or $R^{21}$; and each $R^{21}$ is independently an acyl of a $C_{2-24}$ alkanoic acid or a $C_{4-24}$ alkenoic acid; provided that in each compound of formula IX there is at least one free hydroxy group, and at least one $R^{21}$ group.

10. A composition of claim 5, wherein said surfactant is selected from the group consisting of amphoteric carboxylic imidazoline derivative surfactants, nonionic poly(oxypropylene) poly(oxyethylene) surfactants, and combinations thereof.

11. A composition as recited in claim 10, comprising:
(a) 10 to 15 weight percent sodium chloride and
(b) 5 to 10 weight percent surfactant selected from the group consisting of amphoteric carboxylic imidazoline derivative surfactants, nonionic poly(oxypropylene) poly(oxyethylene) surfactants, and combinations thereof;

(c) 10 to 50 weight percent of an alkylene glycol having between 3 and 8 carbon atoms;

(d) 2 to 30 weight percent of a lower alkanol having 2 to 6 carbon atoms; and (e) an ophthalmologically acceptable solvent;

wherein said composition has a pH of 5 to 6.

12. A composition for simultaneously cleaning and disinfecting contact lenses, consisting essentially of:

(a) about 5 to about 20 weight percent sodium chloride;

(b) about 2 to about 15 weight percent surfactant;

(c) about x to about 50 weight percent of an alkylene glycol having between 3 and 8 carbon atoms;

(d) about y to about 30 weight percent of a lower alkanol having 2 to 6 carbon atoms, wherein x and y are defined by the equation $x/10 + y/2 \geq 1.0$;

(e) 0 to about 2 weight percent pH regulating agent;

(f) a viscosity enhancing agent; and (g) an ophthalmologically acceptable solvent;

wherein said composition is capable of disinfecting and cleaning a contact lens when applied by rubbing said composition for a period less than about 60 seconds.

\* \* \* \* \*